US 6,594,515 B2

(12) United States Patent
Watson

(10) Patent No.: US 6,594,515 B2
(45) Date of Patent: Jul. 15, 2003

(54) NONINVASIVE, INTRAUTERINE FETAL ECG STRIP ELECTRODE

(76) Inventor: Richard L. Watson, 1985 Cougar Trail, McPherson, KS (US) 67460

( * ) Notice: Subject to any disclaimer, the term of this patent is extended or adjusted under 35 U.S.C. 154(b) by 0 days.

(21) Appl. No.: 09/758,626

(22) Filed: Jan. 10, 2001

(65) Prior Publication Data
US 2001/0031915 A1 Oct. 18, 2001

Related U.S. Application Data

(60) Provisional application No. 60/175,359, filed on Jan. 10, 2000.

(51) Int. Cl.[7] ............................................. A61B 5/0448
(52) U.S. Cl. ..................................... 600/376; 600/393
(58) Field of Search ................................. 600/376, 393, 600/511, 391

(56) References Cited

U.S. PATENT DOCUMENTS

| 3,957,036 A | * | 5/1976 | Normann ..................... 600/377 |
| 4,494,552 A | | 1/1985 | Heath |
| 4,501,276 A | | 2/1985 | Lombardi |
| 4,583,549 A | * | 4/1986 | Manoli ........................ 600/391 |
| 5,025,787 A | * | 6/1991 | Sutherland et al. .......... 600/376 |
| 5,184,619 A | * | 2/1993 | Austin ......................... 600/393 |
| 5,199,432 A | | 4/1993 | Quedens et al. |
| 5,341,806 A | * | 8/1994 | Gadsby et al. ............... 600/393 |
| 5,377,673 A | | 1/1995 | Van Dell et al. |
| 5,425,362 A | | 6/1995 | Siker et al. |
| 5,551,424 A | | 9/1996 | Morrison et al. |
| 5,634,459 A | | 6/1997 | Gardosi |
| 5,645,062 A | * | 7/1997 | Anderson et al. ............ 600/391 |
| 5,823,952 A | * | 10/1998 | Levinson et al. ............ 600/376 |

FOREIGN PATENT DOCUMENTS

| DE | 3816190 | * | 8/1989 | .................. 600/376 |
| WO | 93/03669 | * | 3/1993 | .................. 600/376 |

* cited by examiner

Primary Examiner—Lee Cohen
(74) Attorney, Agent, or Firm—Loeffler Jonas & Tuggey LLP

(57) ABSTRACT

A disposable and noninvasive intrauterine fetal monitoring electrode assembly for monitoring fetal heart rate comprises an electrode strip for insertion into the uterus of a woman in active labor, between and in contact with the tissue of the uterine wall and the baby, and an interconnect cable for connecting the assembly to fetal monitoring equipment. The electrode strip comprises a flexible two-sided insulating strip having one or more electrodes disposed on each side of the strip. An electrical connector cable containing electrical leads provides electrical connectivity between each electrode and a separate electrical lead disposed within the connector cable to the fetal monitoring equipment. The electrode strip of the assembly includes a grip feature by which the electrode strip may be engaged to facilitate its positioning in the uterus.

29 Claims, 2 Drawing Sheets

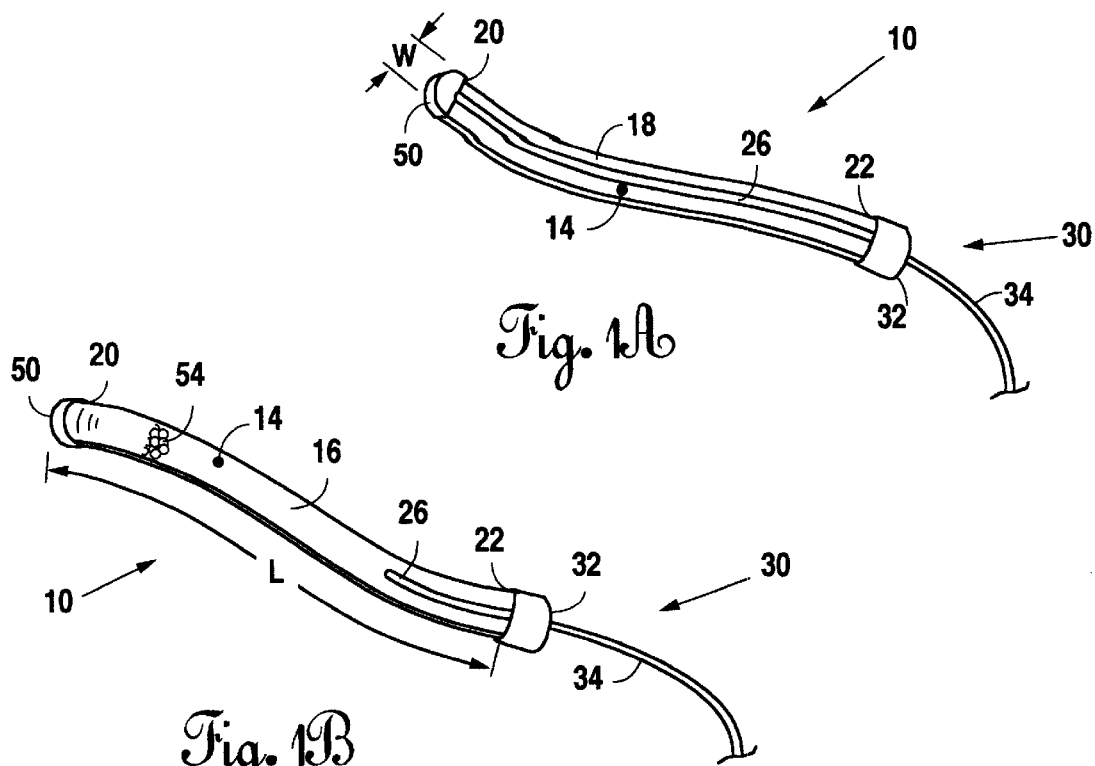
Fig. 1A
Fig. 1B
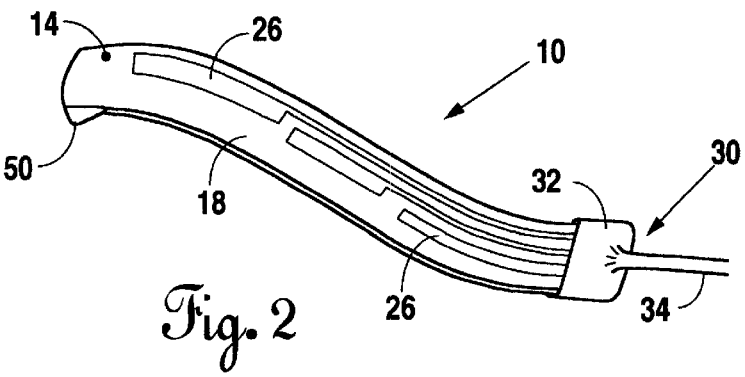
Fig. 2
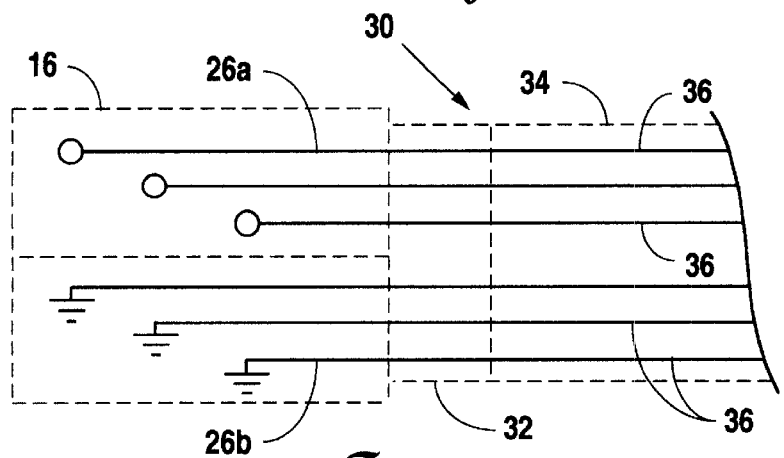
Fig. 3

NONINVASIVE, INTRAUTERINE FETAL ECG STRIP ELECTRODE

The present application claims the benefit of prior filed U.S. Provisional Application, serial No. 60/175,359, filed Jan. 10, 2000, to which the present application is a regular U.S. national application.

FIELD OF THE INVENTION

The present invention is in the field of surgery and devices wherein a specific structure is adapted to be placed in or on a living body for diagnostic purposes. More specifically, the present invention relates to intrauterine ECG electrodes for monitoring a fetus during active labor.

BACKGROUND OF THE INVENTION

During active labor, it is often desirable to continuously monitor certain physiological parameters that are indicative of the condition of the fetus in utero, such as fetal heart rate (FHR). This desirability has motivated the field to develop a variety of intrauterine devices for monitoring FHR, and other fetal physiological parameters (e.g., pH, oxygen tension, etc.) as more serious medical concerns for the fetus' well being may indicate. Examples of such devices include Lumbardi (U.S. Pat. No. 4,501,276), Quedens et al. (U.S. Pat. No. 5,199,432) and Morrison et al. (U.S. Pat. No. 5,551,424), which all describe probes containing an ECG electrode for intrauterine application during active labor, and useful to monitor FHR. However, these electrode probe devices all require the implantation of the electrode into or through the skin (typically, the scalp) of the fetus. Though touted as minimally invasive, and though useful for their intended purpose, such trans-dermally implanted electrodes still present a risk of infection resultant from the lesion the electrode must necessarily make in the skin of the fetus.

To overcome this disadvantage, the field has been further motivated to provide intrauterine fetal monitoring probes that are less invasive than trans-dermal electrodes. For example, Gardosi (U.S. Pat. No. 5,634,459) discloses an intrauterine two sided probe for monitoring a fetus during labor. The Gardosi probe has an elongated body with a skin surface contact electrode on each of its sides, a fetal tissue contact electrode on one side and a maternal tissue contact electrode on the other side. Additionally, the Gardosi electrode has an inflatable balloon element at its distal end to assist in maintaining placement of the probe after it has been positioned, and a hollow passage through the interior of the elongated body for inflating the balloon.

Siker et al. (U.S. Pat. No. 5,425,362) also describe a fetal sensor probe for insertion within the uterus of a woman in active labor. The Siker probe includes a sheath which houses a flexible (spring steel) strip that biases the end of the Siker probe to have an outward curvature relative to the fetus it contacts in the preferred embodiment, or to be flat. The sensors on the Siker probe are encased within the sheath and do not directly contact the fetal tissue.

Another intrauterine fetal monitoring probe is disclosed by Van Dell et al. (U.S. Pat. No. 5,377,673). Van Dell discloses a probe comprising a laminate pad enclosing a light source, one or more sensors and a switch means. The pad is designed to be intra-cervically adhered using an adhesive to the skin of the fetus' face or chest, or to be looped around an extremity. These methods of attaching the Van Dell probe can be relatively cumbersome to accomplish.

Although the above probe devices may be useful for their intended purposes, it would be beneficial in the field to have an alternative fetal monitoring probe electrode that is less invasive than the trans-dermal electrodes, which can provide an ECG wave form in addition to FUR data, and which is simple in design and economical to use.

SUMMARY OF THE INVENTION

The present invention is a disposable intrauterine fetal monitoring electrode assembly. The electrode assembly is for use with fetal monitoring equipment to accurately monitor fetal heart rate (FHR) during labor after the amniotic membrane has been ruptured. The assembly is a thin, flexible strip made of an insulating material with a metallic surface electrode fixed to each side of the strip. Electrical leads or wires separately connect the surface electrodes to the monitoring equipment. The flexible strip portion of the assembly is introduced into the vagina (e.g., during vaginal exam) and advanced through the dilated cervix between the maternal uterine tissue and the fetus' head. The assembly may be held in place by surface features on either or both sides of the strip in combination with the pressure of the uterine sidewall against the electrode assembly.

The electrode assembly comprises a thin, flexible strip having two sides and two ends: an insertion end and a connector end. The material of the flexible strip is an electrical insulator. The insulating strip has two electrodes (or two sets of electrodes), one disposed on each of its sides. The inputs to many ECG machines usually require a minimum of three leads to provide a suitable monitor trace. However, as is known in the art, a two lead ECG electrode may be adapted to provide an appropriate input to an ECG monitor that requires a three lead input. See Heath, U.S. Pat. No. 4,494,552, disclosing a body tissue impedance simulating circuit to adapt a two lead ECG electrode to a three lead ECG monitor input. The electrodes may be disposed in various locations on the strip with a conductor leading from each electrode to the connector end of the strip where it is connected to its own electrical lead for connection to the input of the fetal monitoring equipment. An electrical connector is disposed at the connector end of the flexible strip.

The electrical connector is an insulating sheath containing electrical leads. At its distal end, the electrical connector is attached to the connector end of the insulating strip and adapted to connect the electrodes on both sides of the flexible strip to its respective electrical lead. This provides electrical continuity between each electrode and a separate electrical lead disposed within the insulating sheath of the electrical connector. The proximal end of the electrical connector is adapted to be attachable to an input of the fetal monitor equipment.

The flexible insulating strip of the electrode assembly serves as an insulator separating the electrodes on one side of the strip from those on the other side. The insulating strip may be made of any of a variety of flexible insulator materials to which a metal electrode may be fixed, such as rubber, latex and plastic. MYLAR™ (DuPont de Nemours & Co., Delaware) is a commercially available polyester film that is a particularly desirable electrode assembly strip material, as it is possible to adhere or plate a conductive metal onto a MYLAR™ strip. The plating of silver on to MYLAR™ is already known in the art. However, any electrical conductor that can be fixed to the surfaces of the flexible strip may be adapted for use in the present invention, including stainless steel.

On one side, at the insertion end, a grip feature is fixed to the flexible strip. The purpose of the grip feature is to provide a means for inserting the electrode assembly through the cervical opening and into position between the tissue of the fetus and the uterine wall. The grip feature may be a pocket for releaseably receiving a stylet guide, or simply a finger grip to facilitate positioning the electrode assembly by hand. The flexible strip has a width ranging from about 0.5 cm to about 2.0 cm, and a length ranging from about 4.0 cm to about 10.0 cm.

A set of one or more electrodes are disposed on each surface of the flexible insulating strip. Either side of the insulating strip may have a plurality of electrodes disposed on that side. One set of electrodes of the electrode assembly are the reference electrodes, and the other set serve as the signal electrodes. One side of the insulating strip contacts the maternal tissue of the uterus and has the grip feature disposed at its insertion end. The other side of the flexible strip contacts the tissue of the fetus. The contact electrodes on the side of the flexible strip that interface with the maternal tissue serve as the reference electrodes. Conversely, the electrodes on the side of the flexible strip that interface with the fetal tissue serve as the signal electrodes.

The electrodes of the present invention are contact electrodes as opposed to the implant-type electrodes discussed above. A surface portion of the present contact electrodes interacts at the surface of the tissue it contacts, but does not impale the tissue as does an implant-type electrode. A consideration in the design of an electrode is minimization of the electrode-to-tissue contact impedance between the electrode and the tissue it contacts. Factors influencing contact impedance include the surface area of the electrode, how much of the electrode surface area securely contacts the tissue, and the conductivity or ease with which the electrode material conducts electricity. The flexible insulator strip of the present electrode assembly, especially a MYLAR™ insulator strip with silver plated electrodes, is readily conformable to the surfaces it contacts in the present application. Additionally, the electrode-to-surface contact area and contact impedance of the electrode may be optimized in an assembly having a set of multiple electrodes on one or both sides of the insulator strip by selecting the best positioned electrode in the set, or to interconnect additional electrodes of a set on the one side to increase the effective surface area of the electrode.

To further reduce contact impedance, the tissue contacting surface of the electrodes may be coated with a conductivity enhancing material, such as is known in the art. The conductivity enhancing material may be applied to the electrode by any of a number of means known to one of ordinary skill in the art. Examples of electrode conductivity enhancing materials includes saline gels and chlorides of the desired conductive metal. Ibid.

BRIEF DESCRIPTION OF THE DRAWINGS

FIGS. 1A and 1B are perspective views of the two sides of the fetal intrauterine strip electrode of the present invention showing the side for contacting the fetal tissue (FIG. 1A) and the side for contacting maternal tissue (FIG. 1B).

FIG. 2 is a perspective view of a fetal intrauterine strip electrode of the present invention showing the side for contacting the fetal tissue with multiple electrodes on the surface of that side of the strip.

FIG. 3 is a schematic diagram of the electrical connectivity of a multi-electrode fetal intrauterine strip electrode of the present invention.

DETAILED DESCRIPTION OF THE INVENTION

Figure 4:
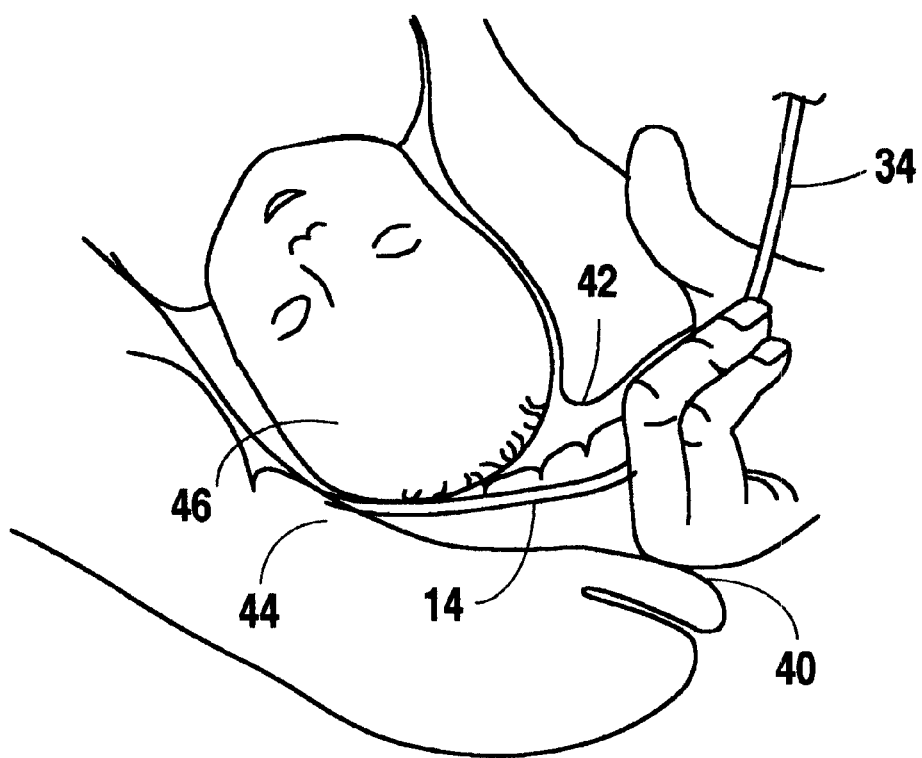
FIG. 4 is a graphic illustration of the manual placement of the flexible strip portion of the present electrode assembly.

Referring now to the drawings, the details of preferred embodiments of the present invention are graphically and schematically illustrated. Like elements in the drawings are represented by like numbers, and any similar elements represented by like numbers with a different lower case letter suffix.

As shown in FIGS. 1A and 1B, the intrauterine fetal monitoring electrode assembly 10 of the present invention is a thin, flexible strip 14 made of an insulating material. The flexible insulating strip 14 has a first side 16, a second side 18, an insertion end 20, a connector end 22, a length L and a width W. The length L of the flexible strip 14 ranges from about 4.0 cm to about 10.0 cm, and the width W from about 0.5 cm to about 2.0 cm. A metallic contact electrode 26 is fixed to each side of the strip 14. The electrodes 26 are disposed on the two sides 16 & 18 of the insulating strip proximate the connector end 22. As shown in FIG. 2, the configuration, positioning and number of the electrodes 26 may vary, but each must electrically project to the connector end 22 of the flexible insulator strip 14.

An electrical connector cable 30, comprising a distal end 32 and an insulating sheath 34 containing electrical leads 36, is attached at its distal end 32 to the connector end 22 of the insulating strip 14. The attachment of the distal end 32 to the insulating strip 14 is adapted to provide electrical connectivity between each electrode 26 and a separate electrical lead 36 disposed within the insulating sheath 34 of the connector cable 30. The proximal end (not shown) of the connector cable 30 is adapted to be attachable to the input of a fetal monitor device, so that a separate electrical lead or wire 36 (see FIG. 3) connects each surface contact electrode 26 to a piece of fetal monitoring equipment (not shown). The piece of fetal monitoring equipment that the proximal end of the electrical connector cable connects to can be an electrode selector switch and/or a two lead to three lead adaptor (e.g., a body tissue impedance simulating circuit).

A grip feature 50 is included on one side of the insulating strip 14 at the insertion end 20. The purpose of the grip feature is to provide a means for inserting the electrode assembly 10 through the cervical opening and into position between the tissue of the fetus and the uterine wall. The grip feature 50 may be a pocket for releaseably receiving a stylet guide (not shown), or simply a finger grip to facilitate positioning the electrode assembly by hand (see FIG. 1B). In use, as shown in FIG. 4, the flexible strip 14 portion of the electrode assembly 10 is introduced into the vagina 40 (e.g., during vaginal exam) and advanced through the dilated cervix 42 between the maternal uterine wall tissue 44 and the fetus' head 46. A finger grip 50 fixed at the insertion end of one side of the flexible insulating strip 14 aids in the insertion of the electrode assembly 10 into position (see FIG. 4). The electrode assembly 10 may be held in place by surface features 54, like "fish scales," on either or both sides of the electrode strip 14 in combination with the pressure of the uterine sidewall 44 against the electrode strip 14.

The electrode assembly 10 comprises a thin, flexible electrode strip 14 having two sides 16 & 18, and serves as an insulator separating the electrodes 26 on one side of the strip from those on the other side. The insulating electrode strip 14 may be made of any of a variety of flexible insulator materials to which a metal electrode may be fixed, such as rubber, latex and plastic. In a preferred embodiment, the electrode strip 14 is a polyester film on which it is possible to adhere or plate a conductive metal. MYLAR™ (DuPont de Nemours & Co., Delaware) is a commercially available polyester film that is a preferred electrode strip material, as the plating of conductive metal on to MYLAR™ is already known in the art. However, any electrical conductor that can be fixed to the surfaces of the flexible strip 14 may be adapted for use as electrodes 26 in the present invention, including stainless steel.

The insulating/electrode strip 14 has two electrodes 26 (or two sets of electrodes), one disposed on each of its sides 16 & 18. The electrodes 26 may be disposed in various locations on the electrode strip 14 with a conductor portion of each electrode 26 leading to the connector end 22 of the strip 14 where it is connected to it own electrical lead 36 for connection to the input of the fetal monitoring equipment. Either side 16 & 18 of the insulating strip 14 may have a plurality of electrodes 26 disposed on that side. One set of electrodes 26 can serve as signal electrodes 26a, and the other set can serve as reference electrodes 26b. (see FIG. 3). One side 16 of the electrode strip 14 contacts the maternal tissue 44 of the uterus and has the grip feature 50 disposed at its insertion end 20. The other side 18 of the flexible electrode strip 14 contacts the fetal tissue 46. The contact electrodes 26 on the side 16 of the flexible strip 14 that interface with the maternal tissue 44 typically serve as the reference electrodes 26b, and the electrodes 26 on the other side 18 of the flexible strip 14 that interface with the fetal tissue 46 serve as the signal electrodes 26a.

The electrical connector 32 of an electrical connector cable 30 is attached to the connector end 22 of the flexible electrode strip 14, and connects the electrodes 26 to the leads 36 of the electrical connector cable 30. In one preferred embodiment, the connection between the strip 14 and the cable 30 is fixed, and the entire electrode assembly 10 is disposable. In an alternative preferred embodiment, the flexible electrode strip 14 is removable or detachable from the connector cable 30, and is separately disposable. This latter embodiment wherein the flexible insulating strip 14 is reversibly detachable from the connector cable 30 allows the electrical connector cable 30 to be reused by attaching a new electrode strip to the connector cable 30.

As shown in FIG. 3, the electrical connector cable 30 has an insulating sheath 34 containing electrical leads 36. An electrical connector 32 at the distal end of the connector cable 30 is attached to the connector end 22 of the insulating strip 14 and adapted to connect the electrodes on both sides of the flexible strip to its respective electrical lead. This provides electrical continuity between each electrode 26 and a separate electrical lead 36 disposed within the insulating sheath 34 of the electrical connector cable 30. The proximal end (not shown) of the electrical connector cable 30 is adapted to be attachable to an input of the fetal monitor equipment.

As noted above, the electrodes 26 of the present invention are contact-type electrodes. The present contact electrodes 26 are noninvasive, relative to the implant-type electrodes discussed above, in that they interact at the surface of the tissue they contact, and do not impale the tissue as do implant-type electrodes. To minimize the electrode-to-tissue contact impedance, the electrodes 26 have a sufficient surface area. How much surface area is sufficient is readily discernable by one of ordinary skill in the art. Certain prior ECG electrodes are about 1.0 cm circles. The length L and width W dimensions of the present flexible electrode strip 14 is more than ample to provide for electrodes 26 having surface areas equivalent to those currently practiced in the field. To further improve electrical characteristics of the electrode assembly 10, the dimensions of the electrode strip 14 allow an electrode 26 on one side of the strip 14 to be laterally displaced from the electrode 26 on the other side of the strip to increase the range of distances that the electrodes 26 can be spatially displaced. Because spatial displacement of the electrodes is not necessarily dependant on the thickness of the insulating strip 14, the thickness of the strip may be made very thin, and the strip 14 itself very ribbon-like. A ribbon-like aspect of the flexible electrode strip 14 enhances the ability of the electrodes 26 on the strip 14 to securely contact the tissue to improve the contact impedance characteristics of the electrode assembly 10. A MYLAR™ insulator strip 14 with silver plated electrodes 26 particularly embodies these benefits.

Figure 5:
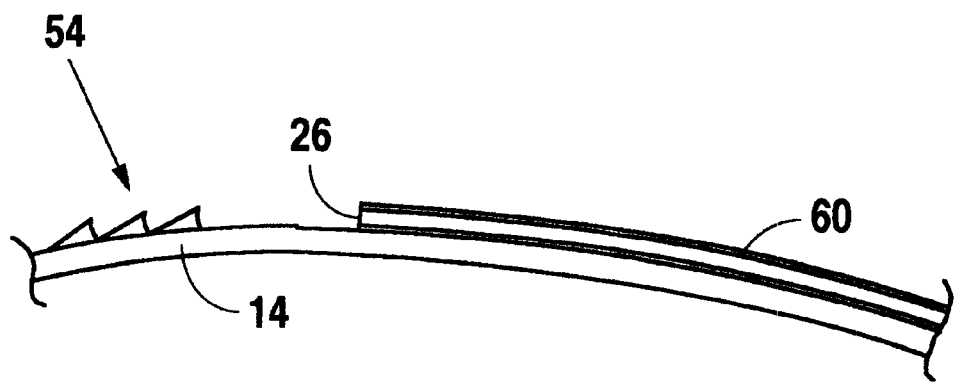
FIG. 5 is a side view of a portion of a flexible electrode strip.

To further optimize the electrode-to-surface contact area and contact impedance characteristics of the electrode assembly 10, sets of multiple electrodes 26 may be disposed on one or both sides of the insulator strip 14. By using a switching circuit (not shown) on the input to the fetal monitoring equipment (not shown) the best positioned electrode 26 or combination of electrodes 26 in the set, may be selected to increase the effective surface area of the electrode 26, reduce contact impedance or otherwise optimize the input signal the monitoring equipment. As shown in FIG. 5, the tissue contacting surface of an electrode 26 may be coated with a conductivity enhancing material 60, such as is known in the art and described above.

While the above description contains many specifics, these should not be construed as limitations on the scope of the invention, but rather as exemplifications of one or another preferred embodiment thereof. Many other variation are possible, which would be obvious to one skilled in the art. Accordingly, the scope of the invention should be determined by the scope of the appended claims and their equivalents, and not just by the embodiments.

What is claimed is:

1. An intrauterine fetal monitoring electrode assembly comprising:
   a ribbon-like insulating strip having a first and a second side on which to mount electrodes, and having an insertion end and a connector end;
   a first electrode disposed on the first side of the insulating strip proximate the connector end;
   a second electrode disposed on the second side of the insulating strip proximate the connector end; and
   an electrical connector cable being an insulating sheath containing electrical leads, the electrical connector cable having a distal end attached to the connector end of the insulating strip and adapted to provide electrical connectivity between each electrode and a separate electrical lead disposed within the insulating sheath, and a proximal end adapted to be attachable to an input of a fetal monitor.

2. The electrode assembly of claim 1, wherein the insulating strip is a polyester film.

3. The electrode assembly of claim 1, wherein the first and the second electrodes are plated onto the insulating strip.

4. The electrode assembly of claim 1, wherein the first and the second electrodes are adhered to the insulating strip.

5. The electrode assembly of claim 1, wherein the insulating strip is polyester film and the electrodes are silver plated onto the polyester film strip.

6. The electrode assembly of claim 1, further comprising a finger grip fixed at the insertion end of one side of the insulating strip.

7. The electrode assembly of claim 1, wherein either of the sides of the insulating strip has a plurality of electrodes disposed on that side.

8. The electrode assembly of claim 1, wherein the strip has a width ranging from about 0.5 cm to about 2.0 cm, and a length ranging from about 4.0 cm to about 10.0 cm.

9. The electrode assembly of claim 1, wherein the electrodes have a tissue contacting surface comprising a layer of a conductivity enhancing material.

10. The electrodes of claim 9, wherein the conductivity enhancing material is a chloride of a conductive metal.

11. The electrode assembly of claim 1, wherein the electrode assembly is disposable.

12. The electrode assembly of claim 1, wherein the insulating strip for mounting electrodes is reversibly detachable from the connector cable and is separately disposable.

13. The electrode assembly of claim 1, wherein the electrodes are contact electrodes.

14. The electrode assembly of claim 1, wherein the first electrode and/or the second electrode is a set of a plurality of electrodes.

15. The electrode assembly of claim 1, wherein at least one of said first and second sides of said insulating strip comprises surface features for helping to hold said assembly in place between fetal tissue and maternal tissue.

16. The electrode assembly of claim 15, wherein said surface features comprise protuberances resembling fish scales.

17. An intrauterine fetal monitoring electrode assembly comprising:
   a ribbon-like insulating strip having a first side and a second side;
   a first electrode disposed on said first side of said insulating strip;
   a second electrode disposed on said second side of said insulating strip,
   a Erat electrical lead connected to said first electrode and having a proximal end attachable to an input of a fetal monitor; and
   a second electrical lead connected to said second electrode and having a proximal end attachable to an input of a fetal monitor.

18. The electrode assembly of claim 17, wherein said insulating strip comprises a polyester film.

19. The electrode assembly of claim 17, wherein said first and second electrodes comprise silver plated onto said insulating strip.

20. The electrode assembly of claim 17, wherein at least one of said first and second electrodes comprises a plurality of electrodes.

21. The electrode assembly of claim 17, wherein at least one of said first and second electrodes comprises a layer of a conductivity enhancing material.

22. The electrode assembly of claim 17, wherein at least one of said first and second sides of said insulating strip comprises surface features for helping to hold said assembly in place between fetal tissue and maternal tissue.

23. The electrode assembly of claim 22, wherein said surface features comprise protuberances resembling fish scales.

24. An intranterijie fetal monitoring electrode assembly comprising:
   a ribbon-like insulating strip having a first side with a first electrode disposed thereon, a second side with a second electrode disposed thereon. and a grip for aiding in placement of said insulating strip between a fetus and a uterine wall, at least one of said first and second sides of said insulating strip comprising protuberances for helping to hold said insulating strip in place between the fetus and the uterine wall; and
   first and second electrical leads respectively connected to said first and second electrodes, each of said first and second electrical leads having a proximal end attachable to an input of a fetal monitor.

25. The electrode assembly of claim 24, wherein said insulating strip comprises a polyester film.

26. The, electrode assembly of claim 24, wherein said first and second electrodes comprise silver plated onto said insulating strip.

27. The electrode assembly of claim 24, wherein at least one of said first and second electrodes comprises a plurality of electrodes.

28. The electrode assembly of claim 24, wherein at least one of said first and second electrodes comprises a layer of a conductivity enhancing material.

29. The electrode assembly of claim 24, wherein said protuberances resemble fish scales.

* * * * *

UNITED STATES PATENT AND TRADEMARK OFFICE
CERTIFICATE OF CORRECTION

PATENT NO. : 6,594,515 B2  
DATED : July 15, 2003  
INVENTOR(S) : Richard L. Watson It is certified that error appears in the above-identified patent and that said Letters Patent is hereby corrected as shown below:

<u>Column 7,</u>
Line 38, the fourth element should read -- a first electrical lead . . . -- rather than "a Erat electrical lead . . .";

<u>Column 8,</u>
Line 17, the word "intranterijie" in the preamble should be -- intrauterine --;
Line 21, the period should be a comma;
Line 33, there should be no comma after the word "The".

Signed and Sealed this

Twentieth Day of January, 2004

JON W. DUDAS
*Acting Director of the United States Patent and Trademark Office*